(12) United States Patent
Kobayashi

(10) Patent No.: US 8,871,440 B2
(45) Date of Patent: Oct. 28, 2014

(54) METHOD FOR EVALUATION OF TISSUE PRESERVATION SOLUTION

(75) Inventor: Eiji Kobayashi, Wakayama (JP)

(73) Assignees: Otsuka Pharmaceutical Factory, Inc., Tokushima (JP); Jichi Medical University, Tochigi (JP)

(*) Notice: Subject to any disclaimer, the term of this patent is extended or adjusted under 35 U.S.C. 154(b) by 613 days.

(21) Appl. No.: 12/450,116

(22) PCT Filed: Jan. 18, 2008

(86) PCT No.: PCT/JP2008/050599
§ 371 (c)(1),
(2), (4) Date: Oct. 15, 2009

(87) PCT Pub. No.: WO2008/126430
PCT Pub. Date: Oct. 23, 2008

(65) Prior Publication Data
US 2010/0028883 A1    Feb. 4, 2010

(30) Foreign Application Priority Data
Mar. 13, 2007   (JP) ................................ 2007-064171

(51) Int. Cl.
| | | |
|---|---|---|
| *C12Q 1/68* | (2006.01) | |
| *A01N 1/00* | (2006.01) | |
| *C12Q 1/00* | (2006.01) | |
| *G01N 33/50* | (2006.01) | |
| *C12Q 1/66* | (2006.01) | |

(52) U.S. Cl.
CPC .......... *C12Q 1/6816* (2013.01); *G01N 33/5082* (2013.01); *C12Q 1/66* (2013.01)
USPC ................. 435/6.1; 435/1.1; 435/4; 536/22.1

(58) Field of Classification Search
USPC ....................... 435/1.1, 4, 6.1; 536/23.1, 24.3
See application file for complete search history.

(56) References Cited

U.S. PATENT DOCUMENTS

| | | | |
|---|---|---|---|
| 6,365,338 B1 * | 4/2002 | Bull et al. ........................ | 435/1.1 |
| 2003/0054569 A1 * | 3/2003 | Cheng et al. ................... | 436/516 |
| 2004/0096813 A1 | 5/2004 | Baust et al. | |
| 2005/0042692 A1 | 2/2005 | Star et al. | |
| 2006/0251638 A1 * | 11/2006 | Guenzler-Pukall et al. . | 424/94.4 |
| 2010/0249547 A1 * | 9/2010 | Braig et al. .................... | 600/310 |

FOREIGN PATENT DOCUMENTS

| | | |
|---|---|---|
| EP | 0 580 444 | 1/1994 |
| EP | 1 759 582 | 3/2007 |
| JP | 6-40801 | 2/1994 |
| JP | 8-325101 | 12/1996 |
| WO | 98/14605 | 4/1998 |
| WO | 00/02572 | 1/2000 |
| WO | 2005/115141 | 12/2005 |

OTHER PUBLICATIONS

Soriano, P. Nature Genetics 21 : 70-71 (1999).*
Greer III et al., Imaging of light emission from the expression of luciferases in living cells and organisms: a review. Luminescence 17 :43 (2002).*
Coombe et al., Expressed luciferase viability assay (ELVA) for the measurement of cell growth and viability. Journal of Immunological Methods 215 :145(1998).*
Hakamata et al., A transgenic rat with ubiquitous expression of firefly luciferase gene. Proc. of SPIE 6098 :60980G-1 to 60980G-8 (2006).*
Mathew et al., Cell preservation in reparative and regenerative medicine: evolution of individualized solution composition. Tissue Engineering 10 (11/12) :1662 (2004).*
Muhlbacher et al., Preservation Solutions for Transplantation. Transplantation Proceedings 31 :2069 (1999).*
Van Buskirk et al., Hypothernic Storage and Cryopreservation. BioProcess International (Nov. 2004).*
J. Lippincott-Schwartz et al., "Development and Use of Fluorescent Protein Markers in Living Cells", Science, vol. 300, pp. 87-91, Apr. 4, 2003.
H. Inoue et al., "Development of new inbred transgenic strains of rats with LacZ or GFP", Biochemical and Biophysical Research Communications, vol. 329, pp. 288-295, 2005.
Y. Hakamata et al., "'Firefly Rats' as an Organ/Cellular Source for Long-Term In Vivo Bioluminescent Imaging", Transplantation, vol. 81, No. 8, pp. 1179-1184, Apr. 27, 2006.
C. H. Contag et al., "Advances in In Vivo Bioluminescence Imaging of Gene Expression", Annu. Rev. Biomed. Eng., vol. 4, pp. 235-260, 2002.
P. R. Contag et al., "Bioluminescent indicators in living mammals", Nature Medicine, vol. 4, No. 2, pp. 245-247, Feb. 1998.
T. Murakami et al., "Color-engineered rats and luminescent LacZ imaging: a new platform to visualize biological processes", Journal of Biomedical Optics, vol. 10, No. 4, pp. 041204-1-041204-11, Jul./Aug. 2005.
International Search Report issued Feb. 12, 2008 in International (PCT) Application No. PCT/JP2008/050599 and translation of Written Opinion.

(Continued)

*Primary Examiner* — Ethanj Whisenant
(74) *Attorney, Agent, or Firm* — Wenderoth, Lind & Ponack, L.L.P.

(57) ABSTRACT

The present invention provides a method for evaluating preservative effect of a tissue preservation solution, comprising immersing a mammalian tissue introduced with a luminescence or fluorescence labeling gene in the tissue preservation solution, measuring a luminescence or fluorescence level by the labeling gene in the tissue after immersion, and evaluating the preservative effect of the tissue preservation solution based on the luminescence or fluorescence level.

17 Claims, 7 Drawing Sheets

(56) References Cited

OTHER PUBLICATIONS

Supplementary European Search Report in Application No. EP 08 70 3449 dated Apr. 22, 2010.

D. G. M. Molin et al., "A Preservation Method Supporting Multipurpose Analysis of Long-Stored Samples", Cell Preservation Technology, vol. 4, No. 1, pp. 46-50, 2006.

C. J. Fregeau et al., "AmpFℓ STR® Profiler Plus™ and AmpFℓ STR® COfiler™ Analysis of Tissues Stored in GenoFix™, a New Tissue Preservation Solution for Mass Disaster DNA Identification", Journal of Forensic Sciences, vol. 46, No. 5, pp. 1180-1190, 2001.

I. Barash et al., "Real-Time Imaging of β-Lactoglobulin-Targeted Luciferase Activity in the Mammary Glands of Transgenic Mice", Molecular Reproduction and Development, vol. 61, No. 1, pp. 42-48, 2002.

T. Murakami et al., "Genetic Modification in Organ Transplantation and in vivo Luciferase Imaging", Proc. SPIE Int. Soc. Opt. Eng., vol. 5704, pp. 169-176, 2005.

\* cited by examiner

METHOD FOR EVALUATION OF TISSUE PRESERVATION SOLUTION

This application is a U.S. national stage of International Application No. PCT/JP2008/050599 filed Jan. 18, 2008.

TECHNICAL FIELD

The present invention relates to a method for evaluating a tissue preservation solution.

BACKGROUND ART

At present, various tissue preservation solutions have been developed and used in transplantation therapy. For development of tissue preservation solutions, components and composition of a new tissue preservation solution are determined, a tissue (organ) isolated from an animal such as rat and the like is immersed in the preservation solution, and the preserved tissue is transplanted to the animal or biochemically evaluated to determine the preservative effect. Therefore, evaluation of the preservative effect of one preservation solution takes an extremely long time, which makes it difficult to rapidly develop a new tissue preservation solution. Accordingly, there is a demand for the development of a method for evaluating a preservative effect of a tissue preservation solution more rapidly and more conveniently.

In the meantime, recent progress in the imaging strategy that explicitly shows real-time biological events in a cell and a molecule has enabled easy understanding of biological process expressed in living animals. The development of molecular tag such as green fluorescent protein (GFP) derived from jellyfish (*Aequorea victoria*), luciferase derived from firefly (*Photinus pyralis*) and the like has promoted revolution in the past 10 years, and enabled association of complicated biochemical processes with action of protein in live cells (non-patent documents 1, 2). In particular, imaging using luminescence light offers an important opportunity to study various biological processes in live cells (non-patent documents 2, 3). Bioluminescence light reporters show considerably high signal to noise ratios in mammal tissues, based on which light signals released in normal animals can be quantified by noninvasive measurement methods. The present inventors have heretofore developed GFP transgenic rat, LacZ transgenic rat and luciferase transgenic rat, and reported that graft rejection can be easily observed using tissues derived from these rats (non-patent documents 4, 5).

Non-patent document 6 discloses that GFP emits strong fluorescence even after the death of the cells derived from GFP transgenic rat.

non-patent document 1: Science, vol. 300(5616), p. 87, 2003
non-patent document 2: Nat. Med., vol. 4(2), p. 245, 1998
non-patent document 3: Annu. Rev. Biomed. Eng., vol. 4, p. 235, 2002
non-patent document 4: Biochem. Biophys. Res. Commun., vol. 329(1), p. 288, 2005
non-patent document 5: Transplantation, vol. 81, No. 8, p. 1179-1184, 2006
non-patent document 6: J. Biomed. Opt., vol. 10(4), p. 41204, 2005

DISCLOSURE OF THE INVENTION

Problems to be Solved by the Invention

An object of the present invention is to provide a method for evaluating preservative effect of a tissue preservation solution rapidly and conveniently.

Means of Solving the Problems

The present inventors have conducted intensive studies in an attempt to achieve the above-mentioned object and found that preservative effect of a tissue preservation solution can be evaluated in real time by preserving a tissue introduced with a luminescence or fluorescence labeling gene such as luciferase and the like in a tissue preservation solution to be the evaluation target, and measuring the level of luminescence or fluorescence from the preserved tissue, which resulted in the completion of the present invention.

Accordingly, the present invention relates to the following.
[1] A method for evaluating preservative effect of a tissue preservation solution, comprising immersing a mammalian tissue introduced with a luminescence or fluorescence labeling gene in the tissue preservation solution, measuring a luminescence or fluorescence level by the labeling gene in the tissue after immersion, and evaluating the preservative effect of the tissue preservation solution based on the luminescence or fluorescence level.
[2] The method of [1], wherein the labeling gene is luciferase.
[3] The method of [1], wherein the luminescence or fluorescence level in the tissue is measured nondisruptively.
[4] The method of [1], wherein the tissue is isolated from a non-human mammal introduced with the luminescence or fluorescence labeling gene.
[5] The method of [4], wherein the labeling gene is expressed ubiquitously in the mammal.
[6] The method of [4], wherein the target gene is specifically expressed in the object tissue of the mammal.
[7] The method of any of [1] to [6], wherein the tissue preservation solution is a cell preservation solution.
[8] The method of any of [1] to [6], wherein the tissue preservation solution is an organ preservation solution.
[9] The method of [1], wherein the mammalian tissue is a part of an organ.
[10] A method of producing a tissue preservation solution having a confirmed preservative effect, comprising the following steps:
(I) mixing constituent components of a desired tissue preservation solution to give the tissue preservation solution;
(II) separating a part of the tissue preservation solution obtained in (I) as a sample;
(III) immersing a mammalian tissue introduced with a luminescence or fluorescence labeling gene in the sample separated in (II);
(IV) measuring the level of luminescence or fluorescence by the labeling gene in the tissue after immersion;
(V) evaluating the preservative effect of the sample based on the luminescence or fluorescence level; and
(VI) obtaining, as a tissue preservation solution with confirmed preservative effect, the tissue preservation solution from which the sample confirmed to have the desired preservative effect in (V) derives.

Effect of the Invention

Using the method of the present invention, preservative effect of a tissue preservation solution can be evaluated extremely rapidly and conveniently. In addition, using a tissue isolated from a transgenic animal ubiquitously introduced with a luminescence/fluorescence labeling gene, preservative effect on many kinds of tissues can be simultaneously evaluated by conducting a test once. Thus, using the method of the present invention, the speed of development of a tissue preservation solution can be strikingly improved.

BEST MODE FOR CARRYING OUT THE INVENTION

Figure 1:
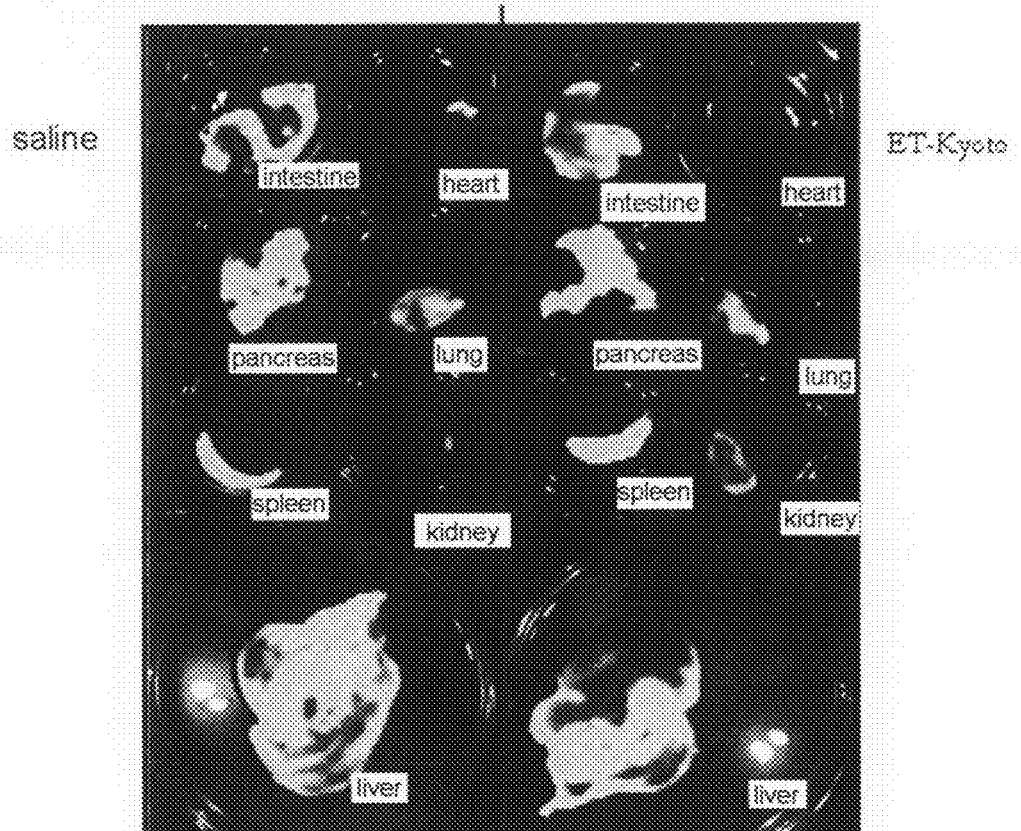
FIG. 1 shows luminescence in each organ (heart, lung, kidney, small intestine, pancreas, spleen, liver) at the start of the preservation (0 hr). left: saline, right: ET-Kyoto solution.
Figure 2:
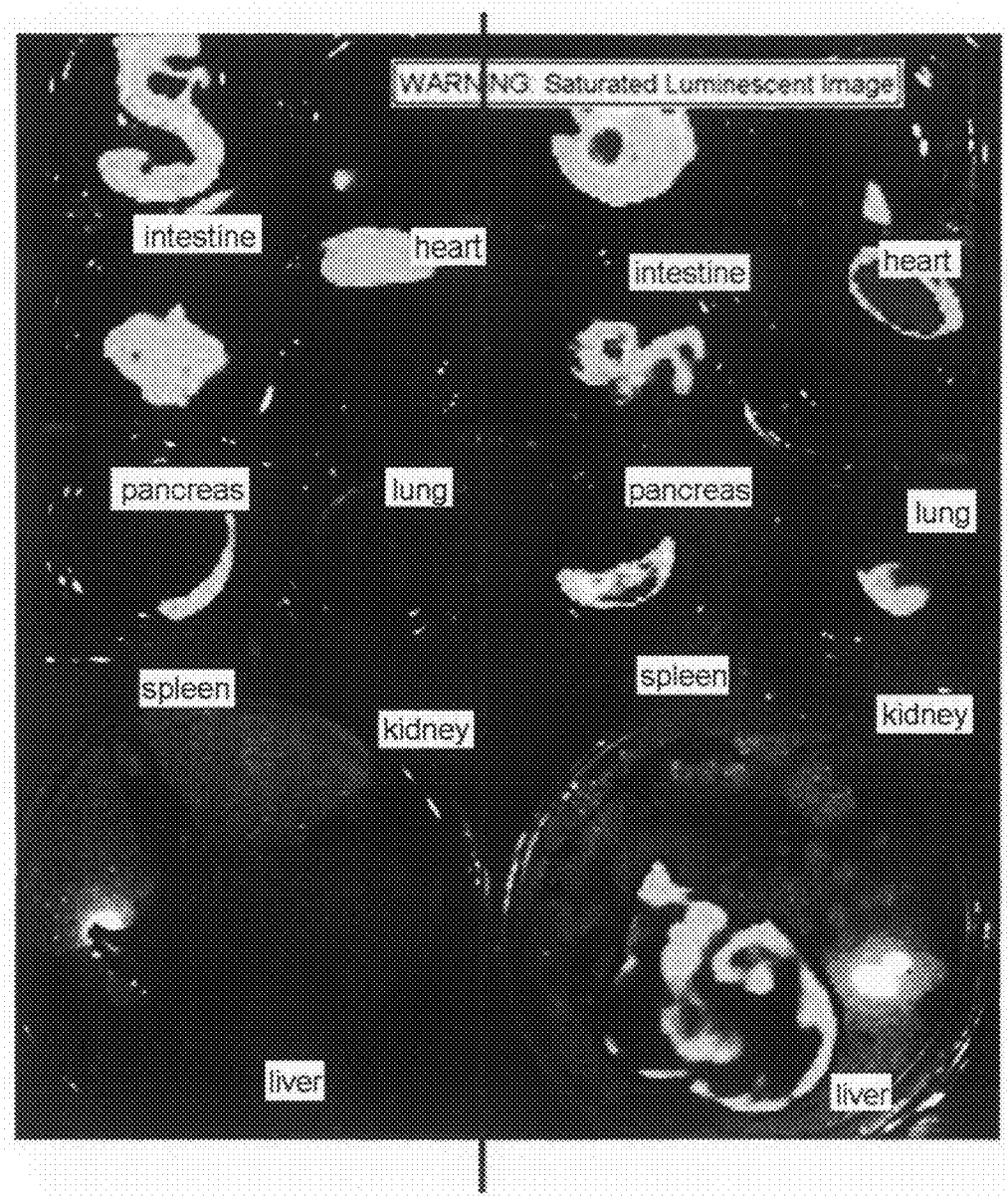
FIG. 2 shows luminescence in each organ at 24 hr after the start of the preservation. left: saline, right: ET-Kyoto solution.
Figure 3:
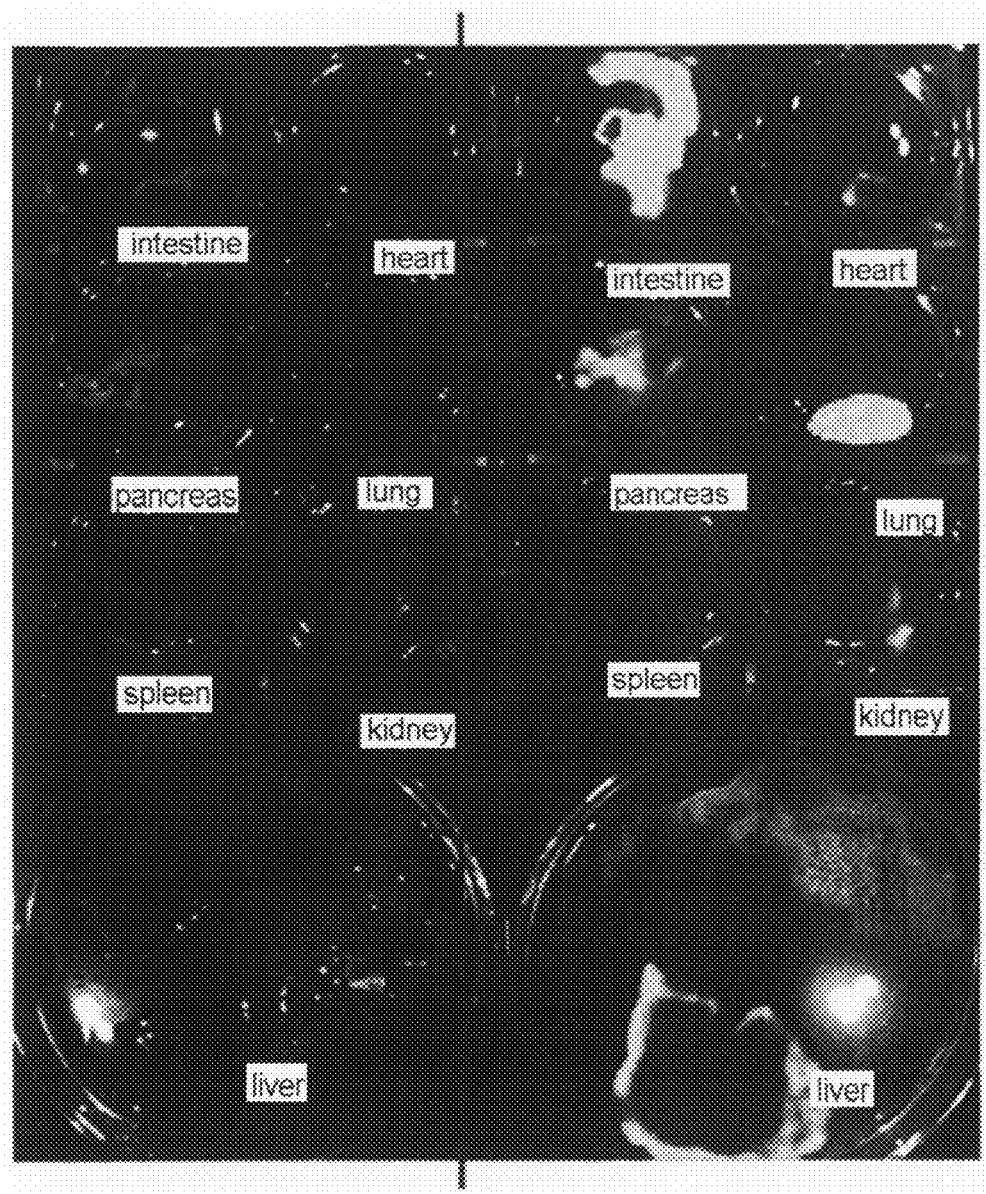
FIG. 3 shows luminescence in each organ at 48 hr after the start of the preservation. left: saline, right: ET-Kyoto solution.

The present invention provides a method for evaluating preservative effect of a tissue preservation solution, comprising immersing a mammalian tissue introduced with a luminescence or fluorescence labeling gene in the tissue preservation solution, measuring a luminescence or fluorescence level by the labeling gene in the tissue after immersion, and evaluating the preservative effect of the tissue preservation solution based on the luminescence or fluorescence level.

In the method of the present invention, a mammalian tissue introduced with a luminescence or fluorescence labeling gene is used.

The luminescence or fluorescence labeling gene to be used in the method of the present invention includes a gene encoding a protein having luminescence or fluorescence, and a gene encoding an enzyme emitting luminescence or fluorescence when mixed with the corresponding luminescent or fluorescent substrate. Examples of the former include a gene encoding fluorescent protein such as GFP, RFP, YFP, CFP, EGFP and the like. Examples of the latter include a gene encoding an enzyme such as luciferase, β-galactosidase, peroxidase and the like. Examples of the substrate (luminescent) of luciferase include luciferin (and ATP as necessary) and the like. Examples of the substrate (luminescent) of β-galactosidase include a luciferin galactoside substrate (6-O-β-galactopyranosyl luciferin) and the like. Examples of the substrate of peroxidase include luminal (and hydrogen peroxide as necessary) and the like. From the aspects of sensitivity and the like, the labeling gene is preferably a luminescence-labeling gene. As the luminescence-labeling gene, a gene encoding the above-mentioned enzyme is preferable, and as the enzyme, luciferase is particularly preferable. GFP emits strong fluorescence even after the death of the cell (J. Biomed. Opt., vol. 10(4), p. 41204, 2005). However, since the luciferase activity well reflects the viability of the tissue, the preservative effect of a tissue preservation solution can be evaluated at high sensitivity using a luciferase gene as a labeling gene.

During organ preservation, depletion of ATP in the organ (cell) in the initial stages is one of the causes of the death of the cells in a tissue. Therefore, ATP concentration of the tissue is an important factor that influences the tissue viability. Luciferase oxidizes luciferin in an ATP-dependent manner to emit luminescence. Luciferase in the tissue can react with luciferin, and emit luminescence reflecting the residual ATP level of the tissue. Thus, using luciferase as a labeling gene, highly sensitive evaluation of the preservative effect of a tissue preservation solution also reflecting the residual ATP level of the tissue is possible.

Examples of the mammal include rodents such as mouse, rat, hamster, guinea pig and the like, experimental animals such as rabbit and the like, domestic animals such as swine, bovine, goat, horse, sheep, mink and the like, pets such as dog, cat and the like, primates such as human, monkey, *Macaca mulatta*, marmoset, orangutan, chimpanzee etc. and the like.

The tissue includes any organ desired to be preserved in a preservation solution (e.g., brain, spinal cord, stomach, pancreas, kidney, liver, thyroid gland, bone marrow, skin, muscle, lung, gastrointestinal tract (e.g., large intestine, small intestine), blood vessel, heart, thymus, spleen, peripheral blood, orchis, ovary, placenta, uterus, bone, skeletal muscle and the like), a part (slice etc.) of organ, cell (e.g., hepatocyte, splenocyte, nerve cell, pancreatic β cell, bone marrow cell, epidermal cell, epithelial cell, endothelial cell, smooth muscle cell, fibroblast, muscle cell, adipocyte, immunocyte (e.g., macrophage, T cell, B cell, natural killer cell, neutrophil, monocyte), chondrocyte, osteocyte, osteoblast, osteoclast, spermatozoon, ovum, fertilized egg, and progenitor cell, stem cell or cancer cell of these cells).

Using a part (slice etc.) of organ as a tissue and immersing same in tissue preservation solutions in a multi-well plate, many kinds of tissue preservation solution samples can be evaluated at once. In this case, therefore, a part of the organ is prepared into a size accommodated in each well of a multi-well plate (e.g., diameter 3-6 mm, weight 10-50 mg) with a tissue slicer and the like.

In the present specification, the tissue preservation solution includes a cell preservation solution and an organ preservation solution.

A luminescence or fluorescence labeling gene can be introduced into a mammalian tissue by a genetic engineering technique known per se. For example, a tissue separated from a mammal is transfected in vitro with a construct (expression vector) wherein the above-mentioned labeling gene is connected to the downstream of a promoter operable in the object tissue, and the tissue is cultivated in a suitable medium, whereby the labeling gene can be introduced in the tissue.

Examples of the transfection method include biological method, physical method, chemical method and the like. Examples of the biological method include a method using a virus vector, a method utilizing a specific receptor, a cell fusion method (HVJ (Hemagglutinating Virus of Japan), polyethylene glycol (PEG), an electric cell fusion method, and a nuclear fusion method (chromosome transfer)). In addition, examples of the physical method include a microinjection method, an electroporation method, and a method using a gene gun (particle gun). Examples of the chemical method include a calcium phosphate precipitation method, a lipofection method, a DEAE-dextran method, a protoplast method, a red blood cell ghost method, a red blood cell membrane ghost method and a microcapsule method.

Examples of the expression vector include plasmid vector, PAC, BAC, YAC, virus vector, retrovirus vector and the like, and an appropriate one can be selected from these.

The kind of the promoter is not particularly limited as long as it can induce or promote the expression of the labeling gene in the tissue introduced with the labeling gene. Examples of the promoter include SRα promoter, CMV promoter, PGK promoter, SV40 promoter, ROSA26 and the like.

The above-mentioned expression vector preferably contains a sequence that terminates transcription of the object mRNA (poly-A, generally called a terminator). In addition, for higher expression of the labeling gene, splicing signal, enhancer region and partial intron of eucaryotic gene can also be connected to the 5' upstream of a promoter region, between a promoter region and a translational region, or 3' downstream of a translational region. In addition, the above-mentioned expression vector can further contain a selection marker gene to be used for the selection of clone stably harboring the introduced labeling gene (e.g., drug resistance gene such as neomycin resistance gene, hygromycin resistance gene, ampicillin resistance gene and the like).

In addition, a tissue isolated from a mammal introduced with a luminescence or fluorescence labeling gene may be used. The mammal can be produced by a genetic engineering technique known per se. For example, a luminescence or fluorescence labeling gene is introduced into a germ cell such as fertilized egg, unfertilized egg, spermatozoon and progenitor cell thereof and the like of a mammal by a gene transfer method such as calcium phosphate coprecipitation method, electroporation method, lipofection method, agglutination method, microinjection method, gene gun (particle gun) method, DEAE-dextran method and the like, and an offspring animal derived from the germ cell is obtained, whereby a mammal introduced with a luminescence or fluorescence labeling gene can be produced.

For transgene into a germ cell, use of a construct (expression vector) wherein the object labeling gene is connected to the downstream of a promoter operable in the target mammalian cell is generally advantageous.

Specifically, an expression vector wherein a polynucleotide containing a labeling gene is connected to the downstream of a promoter operable in the target mammalian cell is microinjected into a fertilized egg etc. of the target mammal and the fertilized egg is transplanted into the uterus of a pseudopregnant animal, whereby a transgenic mammal capable of high expression of a labeling gene can be produced.

Examples of the expression vector include plasmid vector, PAC, BAC, YAC, virus vector, retrovirus vector and the like, and an appropriate one can be selected from these.

The kind of the promoter is not particularly limited as long as the expression of the labeling gene can be induced or promoted in a mammal introduced with the labeling gene. Using a tissue non-specific promoter, a mammal ubiquitously expressing a luminescence or fluorescence labeling gene can be produced. Using a tissue isolated from the mammal, the preservative effect on many kinds of tissues can be simultaneously evaluated by performing a test once. Examples of the tissue non-specific promoter include SRα promoter, CMV promoter, PGK promoter, SV40 promoter, ROSA26, β-actin promoter and the like. Using a tissue specific promoter, moreover, a mammal that specifically expresses a luminescence or fluorescence labeling gene in the object tissue can be produced. For example, a labeling gene can be expressed liver specifically using an α1-AT promoter, skeletal muscle specifically using an α-actin promoter and neuron specifically using an enolase promoter.

The above-mentioned expression vector preferably contains a sequence that terminates transcription of the object mRNA (poly-A, generally called a terminator). In addition, for higher expression of the labeling gene, splicing signal, enhancer region and partial intron of eucaryotic gene can also be connected to the 5' upstream of a promoter region, between a promoter region and a translational region, or 3' downstream of a translational region. In addition, the above-mentioned expression vector can further contain a selection marker gene to be used for the selection of clone stably harboring the introduced labeling gene (e.g., drug resistance gene such as neomycin resistance gene, hygromycin resistance gene, ampicillin resistance gene and the like).

A mammalian tissue can be immersed in an evaluation target tissue preservation solution by a method known in the technical field. Examples of the method include a method including directly immersing a tissue isolated from an animal in a tissue preservation solution, a method including flushing the blood in a tissue with a physiological aqueous solution such as Ringer's solution, saline and the like and immersing the tissue in a tissue preservation solution, a method including perfusing a tissue with a tissue preservation solution, and immersing the tissue in the tissue preservation solution and the like. While the preservation period and preservation temperature can be appropriately set according to the object and the kind of the tissue preservation solution, the preservation period is generally about 1-30 days and the preservation temperature is about 1 to 10° C. (preferably about 1 to 6° C.)

After preservation of a mammalian tissue by immersing in an evaluation target tissue preservation solution for a certain period, the level of luminescence or fluorescence by a luminescence or fluorescence labeling gene in the tissue is measured. The luminescence or fluorescence level may be measured by homogenizing the tissue after immersion, and measuring the level of luminescence or fluorescence in the homogenate, or the level of luminescence or fluorescence in the tissue may be nondisruptively measured. Since the operation is convenient and the tissue after measurement can be successively used for a further evaluation test, the luminescence or fluorescence level can be preferably measured without homogenizing the tissue. The luminescence or fluorescence level can be measured using a device known per se such as a luminometer, a fluorescence spectrophotometer and the like. When the luminescence or fluorescence level is measured nondisruptively, an imaging system capable of detecting luminescence or fluorescence and the like can be used.

When a gene encoding a protein having luminescence or fluorescence is used as a labeling gene, the luminescence or fluorescence of the protein in the tissue after immersion is directly measured. On the other hand, when a gene encoding an enzyme (for example, luciferase) that produces luminescence or fluorescence when mixed with the corresponding luminescent or fluorescent substrate is used as a labeling gene, the tissue after immersion (or homogenate thereof) is contacted with the corresponding substrate (for example, luciferin), whereby luminescence or fluorescence can be measured.

For example, when the luminescence or fluorescence level is nondisruptively measured using the above-mentioned enzyme as a labeling gene, the tissue after immersion is soaked in an aqueous solution containing the corresponding substrate (substrate solution). As the aqueous solution, a physiological solution such as a tissue preservation solution, Ringer's solution, saline and the like can be used. When a tissue preservation solution is used, a tissue after a fluorescence or luminescence level measurement can be successively used for a further evaluation test.

The substrate concentration of a substrate solution is appropriately set within the concentration range generally used by those of ordinary skill in the art. For example, the substrate concentration when luciferin is used as the substrate is generally about 10-1000 μg/ml (for example, 150 μg/ml)

The time from immersion of a tissue in a substrate solution to actual measurement of luminescence or fluorescence can also be set appropriately. When this period is too short, the luminescence or fluorescence level is not sufficient and the sensitivity becomes low. On the other hand, when this period is too long, the substrate is degraded, also resulting in low sensitivity. When this period is too long, moreover, the tissue temperature increases, and a tissue after a fluorescence or luminescence level measurement sometimes becomes difficult for use in a further evaluation test. From such aspect, it is preferable to measure the luminescence or fluorescence level in about 3-30 min (for example, 5 min) after immersion of a tissue in a substrate solution.

The temperature of the substrate solution can be appropriately set within the range permitting enzyme reaction. When the temperature of the substrate solution is too low, enzyme reaction does not proceed, and when the temperature is too high, the enzyme becomes inactivated. From such aspects, the temperature of the substrate solution is generally 1-40° C. When a tissue after a fluorescence or luminescence level measurement is successively used for a further evaluation test, the fluorescence or luminescence level is preferably measured at a comparatively low temperature (for example, about 1-10° C., preferably 1-6° C.) so as to maintain good tissue preservation conditions. In this case, therefore, a gene capable of producing sufficient luminescence or fluorescence even under such low temperature conditions should be selected as a labeling gene. Luciferase reacts with luciferin even under the above-mentioned low temperature conditions and produces sufficient luminescence.

Then, the preservative effect of a tissue preservation solution is evaluated based on the luminescence or fluorescence level. For example, the luminescence or fluorescence level by a luminescence or fluorescence labeling gene in a tissue is measured before immersion operation, the luminescence or fluorescence level after immersion is compared with the level before immersion and the amount of decrease in the luminescence or fluorescence level before and after the immersion is calculated. A smaller amount of decrease in the luminescence or fluorescence level can be judged to show a higher preservative effect of the tissue preservation solution.

Alternatively, the amount of decrease in the luminescence or fluorescence level is measured when a tissue preservation solution is not used (for example, when a physiological aqueous solution hardly having a tissue preservative effect such as saline and the like is used) (negative control). Then, the amount of decrease in the luminescence or fluorescence level of the evaluation target tissue preservation solution is compared with that of the negative control, and when the amount of decrease is smaller than that of the negative control, the evaluation target tissue preservation solution is judged to have a tissue preservative effect.

In the above-mentioned judgment, it is preferable to simultaneously measure the above-mentioned amount of decrease of the luminescence or fluorescence level for a tissue preservation solution known to have a preservative effect (positive control) (e.g., ET-Kyoto solution, UW solution etc.). Using the positive control, it is possible to ensure that the evaluation method of the present invention certainly works well, and the level of the tissue preservative effect of the evaluation target tissue preservation solution can be evaluated based on the comparison with that of positive control.

Using the evaluation method of the present invention, a tissue preservation solution having a new composition can be efficiently developed. In addition, the evaluation method of the present invention is useful for the quality control of a tissue preservation solution during large-scale production of the tissue preservation solution in the factory.

Moreover, the present invention provides a method of producing a tissue preservation solution having a confirmed preservative effect, comprising the following steps:
(I) mixing constituent components of a desired tissue preservation solution to give the tissue preservation solution;
(II) separating a part of the tissue preservation solution obtained in (I) as a sample;
(III) immersing a mammalian tissue introduced with a luminescence or fluorescence labeling gene in the sample separated in (II);
(IV) measuring the level of luminescence or fluorescence by the labeling gene in the tissue after immersion;
(V) evaluating the preservative effect of the sample based on the luminescence or fluorescence level; and
(VI) obtaining, as a tissue preservation solution with confirmed preservative effect, the tissue preservation solution from which the sample confirmed to have the desired preservative effect in (V) derives.

In (I), examples of the constituent components of the tissue preservation solution include, but are not limited to, water, buffers (phosphate, acetate, carbonate, citrate, HEPES etc.), isotonicity agents (sorbitol, glucose, mannitol, trehalose, glycerol, propylene glycol, sodium chloride, potassium chloride etc.), impermeabilizing agents (sodium lactobionate, raffinose), colloid osmotic agents (hydroxyethyl starch, dextran etc.), reactive oxygen eliminating agents (vitamin C, flavonoid, polyphenol, glutathione etc.), antibiotic and the like. For example, water, a buffer and an isotonizing agent are blended to give a tissue preservation solution.

When a tissue preservation solution having a known composition (ET-Kyoto solution, UW solution, Euro-Collins solution, Histidine-tryptophan ketoglutarate solution, Perfadex solution etc.) is to be produced, constituent components based on the determined composition may be blended. When a tissue preservation solution having a new composition is to be developed, constituent components are blended at a desired mixing ratio.

In (II), an amount sufficient for evaluation is separated as a sample from the tissue preservation solution obtained in (I).

The steps (III)-(V) are performed according to the aforementioned evaluation method of the present invention. Here, when a tissue preservation solution having a known composition is to be produced, it is preferable to use, as a positive control, a tissue preservation solution having the same composition as in a lot confirmed to have a certain level of tissue preservative effect.

Then, the tissue preservation solution from which the sample confirmed in (V) to have a certain level of tissue preservative effect is derived can be obtained as a tissue preservation solution having a confirmed preservative effect.

Using the production method of the present invention, a tissue preservation solution having a confirmed preservative effect can be produced stably.

The present invention is explained in more detail in the following by referring to Examples, which are not to be construed as limitative.

EXAMPLES

Example 1

Experimental Method

An appropriate amount of luciferin was dissolved in a test solution (tissue preservation solution or saline) to give a luminescence solution. The luminescence solution had a luciferin concentration of 150 μg/ml. As the tissue preservation solution, ET-Kyoto solution was used. The organs (heart, lung, kidney, intestine, pancreas, spleen, liver) were separated from a Lewis rat introduced with a luciferase gene (Luc-LEW) (Transplantation, vol. 81, No. 8, p. 1179-1184, 2006), the blood in the organs was removed, and the organs were immersed in a luminescence solution at 4° C. Luc-LEW rat ubiquitously expresses luciferase gene (Transplantation, vol. 81, No. 8, 2006). At 5 min after immersion of the organs, the quantity of the luminescence from the organs was measured using a real time in vivo imaging system (IVIS Imaging System, Xenogen). During the measurement of the luminescence quantity, the temperature of the luminescence solution was maintained at 4° C. After measurement of the luminescence quantity, the organs were preserved as they were in a refrigerator (4° C.). After 24, 48 and 72 hr, the luminescence solution was exchanged with a fresh solution, and at 5 min after the exchange, the quantity of luminescence from the organs was measured using IVIS in the same manner as above. The luminescence quantity was digitalized (unit: p/sec/cm$^2$/sr), and the organ preservative effect of the test solution was compared.

Results

Figure 4:
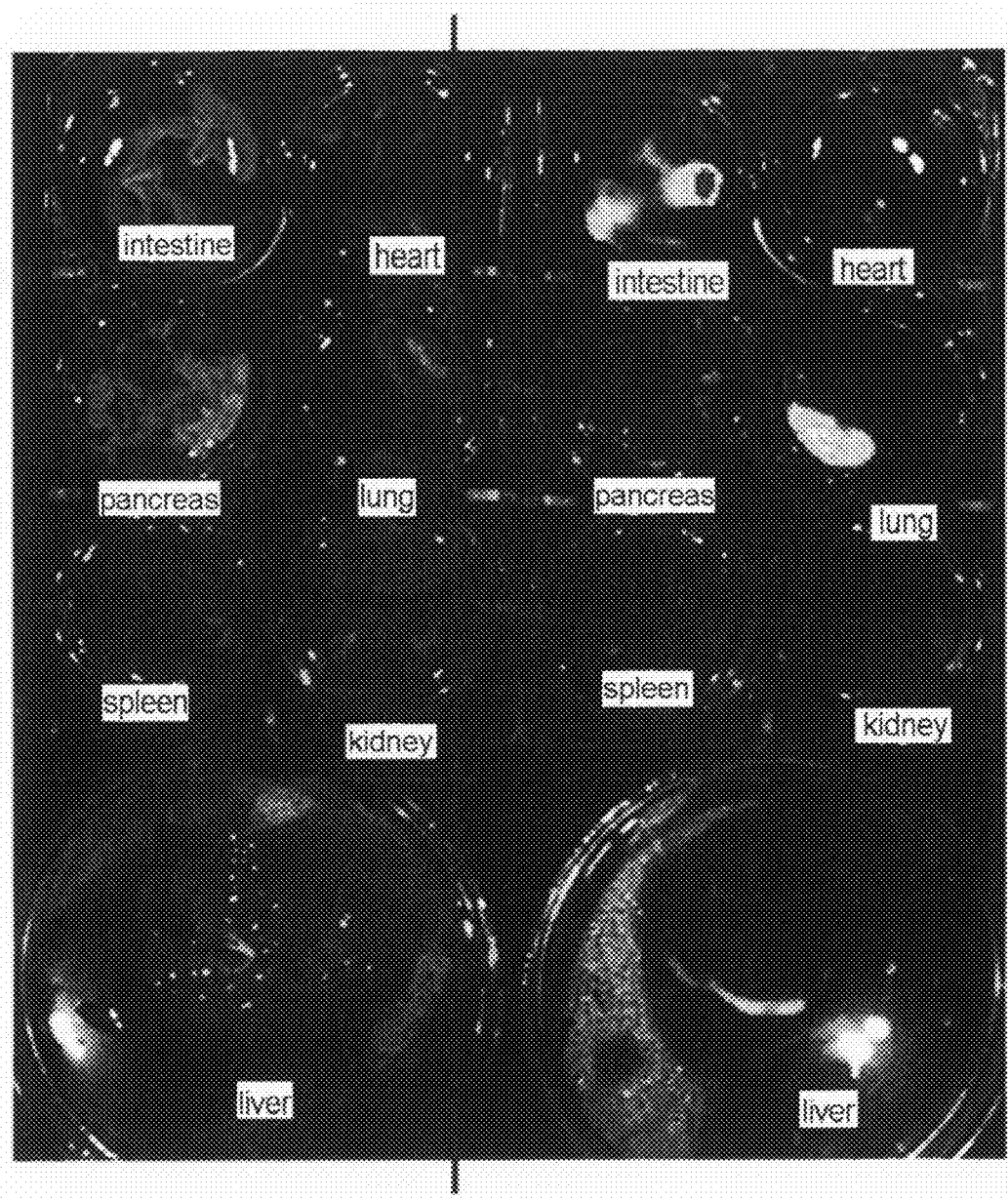
FIG. 4 shows luminescence in each organ at 72 hr after the start of the preservation. left: saline, right: ET-Kyoto solution.
Figure 5:
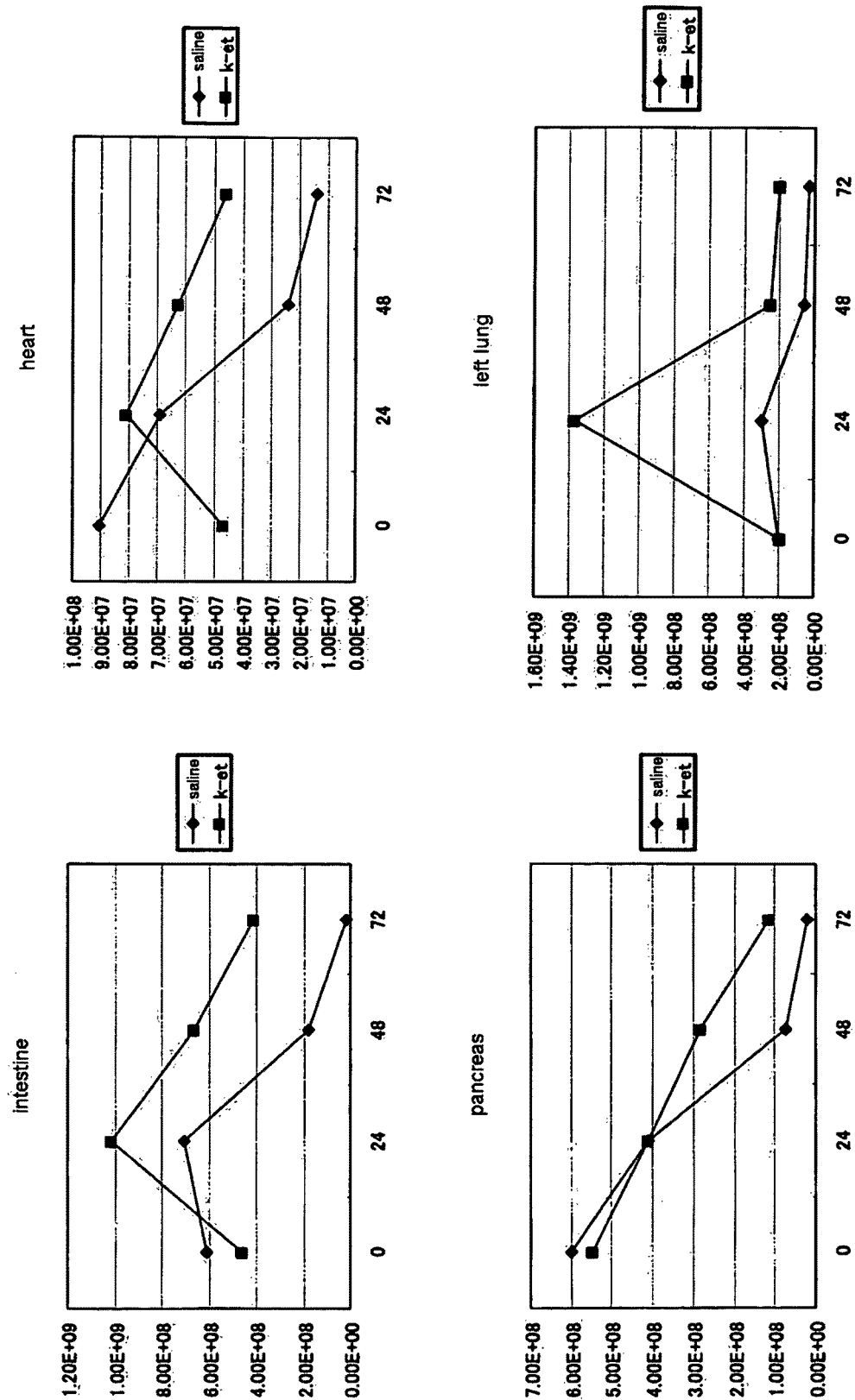
FIG. 5 shows time-course changes in the luminescence levels in small intestine, heart, pancreas and lung. unit: p/sec/cm$^2$/sr, ♦: saline, ■: ET-Kyoto solution.
Figure 6:
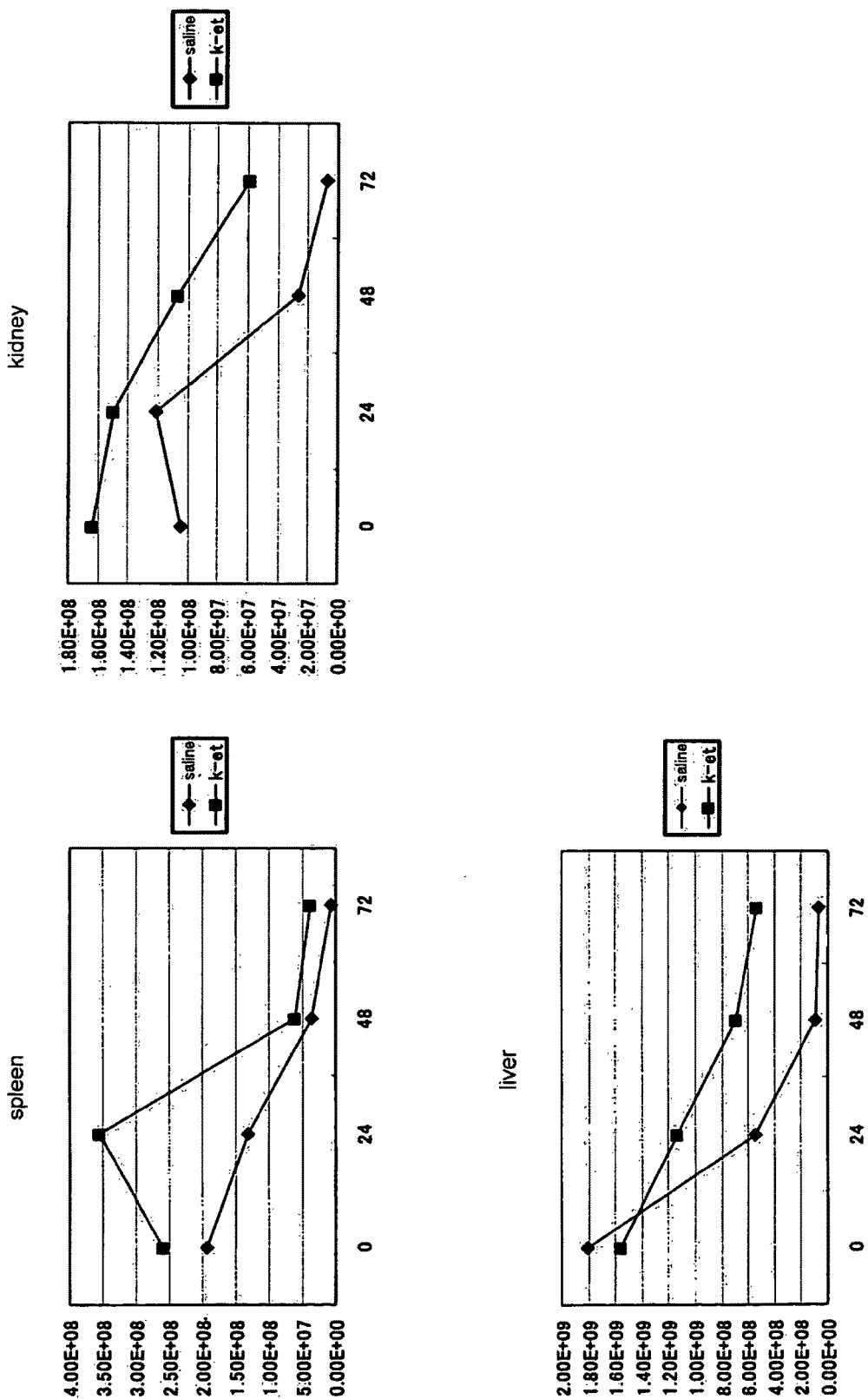
FIG. 6 shows time-course changes in the luminescence levels of spleen, kidney and liver. unit: p/sec/cm$^2$/sr, ♦: saline, ■: ET-Kyoto solution.

The images of luminescence from the organs at 0-72 hr after the start of the preservation are shown in FIGS. 1-4, and the time-course changes in the luminescence quantity in each organ are shown in FIGS. 5 and 6.

At the time of the start of the preservation, the luminescence quantity for ET-Kyoto solution used as the test solution was almost the same as that for saline. However, when each organ was preserved for 72 hr in the saline, luciferase luminescence from the organ was hardly observed. However, when the organ was preserved in the ET-Kyoto solution, significant luciferase luminescence from the organ was still observed (FIGS. 4-6).

From the above results, it was confirmed that the preservative effect of a tissue preservation solution can be evaluated using the luciferase luminescence from the organ as an index.

Example 2

The liver was separated from a Lewis rat introduced with a luciferase gene (Luc-LEW) (Transplantation, vol. 81, No. 8, p. 1179-1184, 2006), the blood in the liver was removed and the liver was protected by ice-cooling (4° C.). The following operation was immediately performed in a room at a low temperature of 4° C. The isolated liver was sliced in a diameter of 3 mm using a tissue slicer. The liver slice was each prepared in a uniform slice of about 14 mg. A test solution (tissue preservation solution or saline) (220 μl) was injected into each well of a 96 well plate, and the liver slice to be examined was immersed in a test solution. As the tissue preservation solution, University of Wisconsin solution, ET-Kyoto solution, Euro-Collins solution, Histidine-tryptophan ketoglutarate solution or Perfadex solution was used. A luciferin solution (20 μl) was added from an injector such that the final concentration of luciferin in the test solution was 190 μg/ml, and the quantity of luminescence from the liver slice was measured using a plate reader (Mithras LB 940, Berthold). After the measurement of the luminescence quantity, the test solution was exchanged to a fresh one and the mixture was preserved at 4° C. until the next measurement. By the above-mentioned method, the luminescence quantity at the start of the preservation (0 hr), and 1, 3 and 6 hr after the start of the preservation was measured, and the organ preservative effects of the test solutions were compared.

Figure 7:
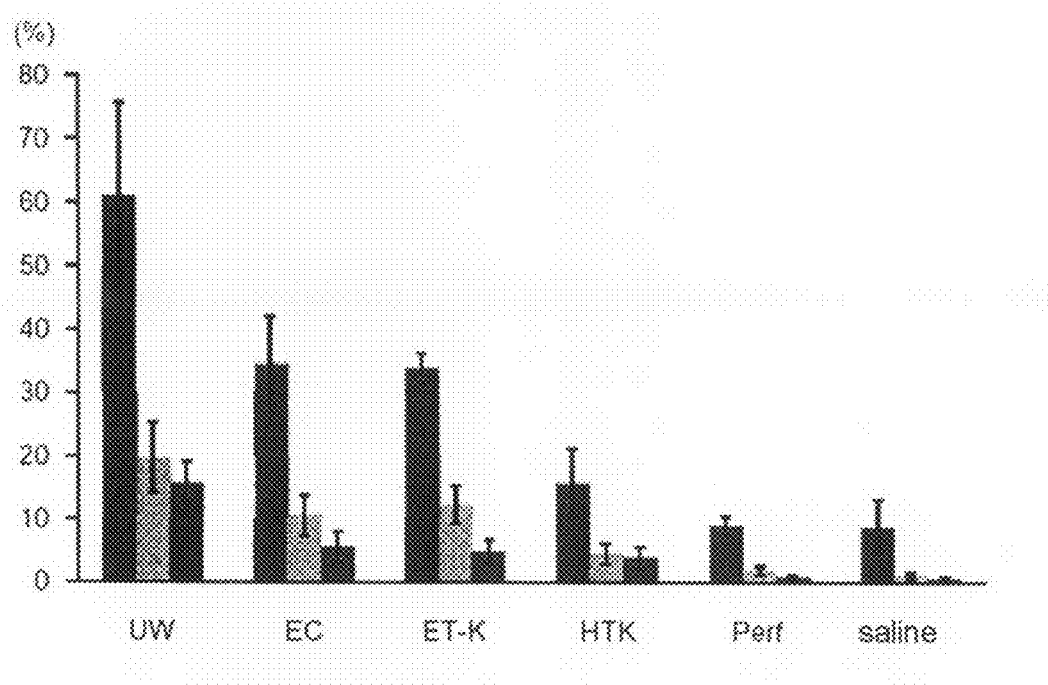
FIG. 7 shows time-course changes in the levels of luminescence from liver slice immersed in various tissue preservation solutions, wherein the luminescence level at the start of the preservation is 100%. Bars show luminescence levels at 1, 3 and 6 hr later from the left. UW: University of Wisconsin solution, EC: Euro-Collins solution, ET-K: ET-Kyoto solution, HTK: Histidine-tryptophan ketoglutarate solution, Perf: Perfadex solution.

The results are shown in FIG. 7.

When the liver slice was preserved in saline, the amount of luminescence of luciferin rapidly decreased. However, when a tissue preservation solution was used, the decrease in the amount of luminescence was mild.

From the above results, it was confirmed that, even when a tissue slice was used, the preservative effect of a tissue preservation solution can be evaluated using the luciferase luminescence from the organ as an index.

INDUSTRIAL APPLICABILITY

Using the method of the present invention, the preservative effect of a tissue preservation solution can be evaluated by a convenient method as compared to the conventional methods.

This application is based on application No. 2007-064171 (filing date: Mar. 13, 2007) filed in Japan, the contents of which are incorporated hereinto by reference.

The invention claimed is:

1. A method for evaluating preservative effect of a tissue preservation solution for preserving mammalian tissue in a live state, comprising immersing a live mammalian tissue introduced with a luciferase gene in the tissue preservation solution, measuring a luminescence level by the luciferase gene in the tissue after immersion by contacting the tissue with a substrate solution containing luciferin and not containing ATP, and evaluating the effect of the tissue preservation solution to preserve the mammalian tissue in a live state based on the luminescence.

2. The method of claim 1, wherein the luminescence level in the tissue is measured nondisruptively.

3. The method of claim 1, wherein the tissue is isolated from a non-human mammal introduced with the luciferase gene.

4. The method of claim 3, wherein the luciferase gene is expressed ubiquitously in the mammal.

5. The method of claim 3, wherein the luciferase gene is specifically expressed in the object tissue of the mammal.

6. The method of claim 1, wherein the tissue preservation solution is a cell preservation solution.

7. The method of claim 1, wherein the tissue preservation solution is an organ preservation solution.

8. The method of claim 1, wherein the mammalian tissue is a part of an organ.

9. A method of producing a tissue preservation solution for preserving mammalian tissue in a live state having a confirmed preservative effect, comprising the following steps:
   (I) mixing constituent components of a desired tissue preservation solution for preserving mammalian tissue in a live state to give the tissue preservation solution;
   (II) separating a part of the tissue preservation solution obtained in (I) as a sample;
   (III) immersing a live mammalian tissue introduced with a luciferase gene in the sample separated in (II);
   (IV) measuring the level of luminescence by the luciferase gene in the tissue after immersion by contacting the tissue with a substrate solution containing luciferin and not containing ATP;
   (V) evaluating the effect of the sample to preserve the mammalian tissue in a live state based on the luminescence level; and
   (VI) obtaining, as a tissue preservation solution with confirmed effect of preserving the mammalian tissue in a live state, the tissue preservation solution from which the sample confirmed to have the desired preservative effect in (V) derives.

10. The method of claim 2, wherein the tissue preservation solution is a cell preservation solution.

11. The method of claim 3, wherein the tissue preservation solution is a cell preservation solution.

12. The method of claim 4, wherein the tissue preservation solution is a cell preservation solution.

13. The method of claim 5, wherein the tissue preservation solution is a cell preservation solution.

14. The method of claim 2, wherein the tissue preservation solution is an organ preservation solution.

15. The method of claim 3, wherein the tissue preservation solution is an organ preservation solution.

16. The method of claim 4, wherein the tissue preservation solution is an organ preservation solution.

17. The method of claim 5, wherein the tissue preservation solution is an organ preservation solution.

\* \* \* \* \*